United States Patent
Kwon et al.

(10) Patent No.: US 10,531,852 B2
(45) Date of Patent: Jan. 14, 2020

(54) DISPLAY FOR CONVERTING MEDICAL IMAGES AND METHOD OF USE

(71) Applicant: SAMSUNG ELECTRONICS CO., LTD., Suwon-si (KR)

(72) Inventors: Jae Hyun Kwon, Hwaseong-si (KR); Hyun Hwa Oh, Hwaseong-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/566,821

(22) Filed: Dec. 11, 2014

(65) Prior Publication Data

US 2015/0178885 A1    Jun. 25, 2015

(30) Foreign Application Priority Data

Dec. 24, 2013 (KR) .......................... 10-2013-0162029

(51) Int. Cl.
*A61B 6/00* (2006.01)

(52) U.S. Cl.
CPC ...... *A61B 6/50* (2013.01); *G06T 2207/20221* (2013.01)

(58) Field of Classification Search
CPC ....... G06T 5/50; G06T 3/0081; G06T 11/001; G06T 13/80; H04N 13/0217; H04N 5/2624; G06K 9/00228; G05D 1/0246; A61B 8/00; A61B 8/468
See application file for complete search history.

(56) References Cited

U.S. PATENT DOCUMENTS

| | | | | |
|---|---|---|---|---|
| 5,657,073 A | * | 8/1997 | Henley | G03B 37/04 348/38 |
| 6,063,030 A | * | 5/2000 | Vara | A61B 8/468 600/437 |
| 6,346,950 B1 | * | 2/2002 | Jouppi | G05D 1/0246 345/660 |
| 8,660,319 B2 | * | 2/2014 | Aarabi | G06K 9/00228 382/100 |

(Continued)

FOREIGN PATENT DOCUMENTS

| | | |
|---|---|---|
| JP | 2003-190134 A | 7/2003 |
| JP | 2006-187412 A | 7/2006 |

OTHER PUBLICATIONS

Shep McAllister, Invert Your Phone's Colors for Easier Night Reading, Nov. 4, 2012.*

(Continued)

*Primary Examiner* — Devona E Faulk
*Assistant Examiner* — Ming Wu
(74) *Attorney, Agent, or Firm* — Sughrue Mion, PLLC

(57) ABSTRACT

A display apparatus is provided to display a plurality of different images with different characteristics of an object on a single screen while gradually and mutually converting the color images and an image display method using the same. The display apparatus includes a memory to store a plurality of color images with different characteristics of an object and a display unit to display a second color image while gradually converting a first color image displayed on the display unit into the second color image, the second color image having a different characteristic from that of the first color image.

21 Claims, 10 Drawing Sheets

(56) References Cited

U.S. PATENT DOCUMENTS

| | | | | |
|---|---|---|---|---|
| 2005/0093875 | A1* | 5/2005 | Zhang | G06T 11/001 |
| | | | | 345/582 |
| 2007/0171192 | A1* | 7/2007 | Seo | H04M 1/72544 |
| | | | | 345/156 |
| 2008/0037851 | A1* | 2/2008 | Takayama | G06T 5/50 |
| | | | | 382/131 |
| 2008/0239423 | A1* | 10/2008 | Kitamura | G03H 1/08 |
| | | | | 359/15 |
| 2009/0131795 | A1* | 5/2009 | Sasaki | A61B 8/00 |
| | | | | 600/443 |
| 2009/0251482 | A1* | 10/2009 | Kondo | H04N 5/2624 |
| | | | | 345/589 |
| 2010/0061612 | A1* | 3/2010 | Reisman | G06T 3/0081 |
| | | | | 382/131 |
| 2012/0294583 | A1* | 11/2012 | Kosaka | G06T 13/80 |
| | | | | 386/230 |
| 2013/0329019 | A1* | 12/2013 | Matsuoka | H04N 13/0217 |
| | | | | 348/49 |
| 2014/0132834 | A1* | 5/2014 | Kondo | G06T 3/40 |
| | | | | 348/441 |

OTHER PUBLICATIONS

X-RayComputedTomography, X-ray computed tomography, Oct. 17, 2013.*
Matlabfreecod, Detection of Vessels in Eye Retina Using Line Tracking Algorithm With Matlab, Feb. 27, 2013.*
X-ray computed tomography, Oct. 17, 2013 (Year: 2013).*
Detection of Vessels in Eye Retina Using Line Tracking Algorithm With Matlab, Feb. 27, 2013 (Year: 2013).*

* cited by examiner

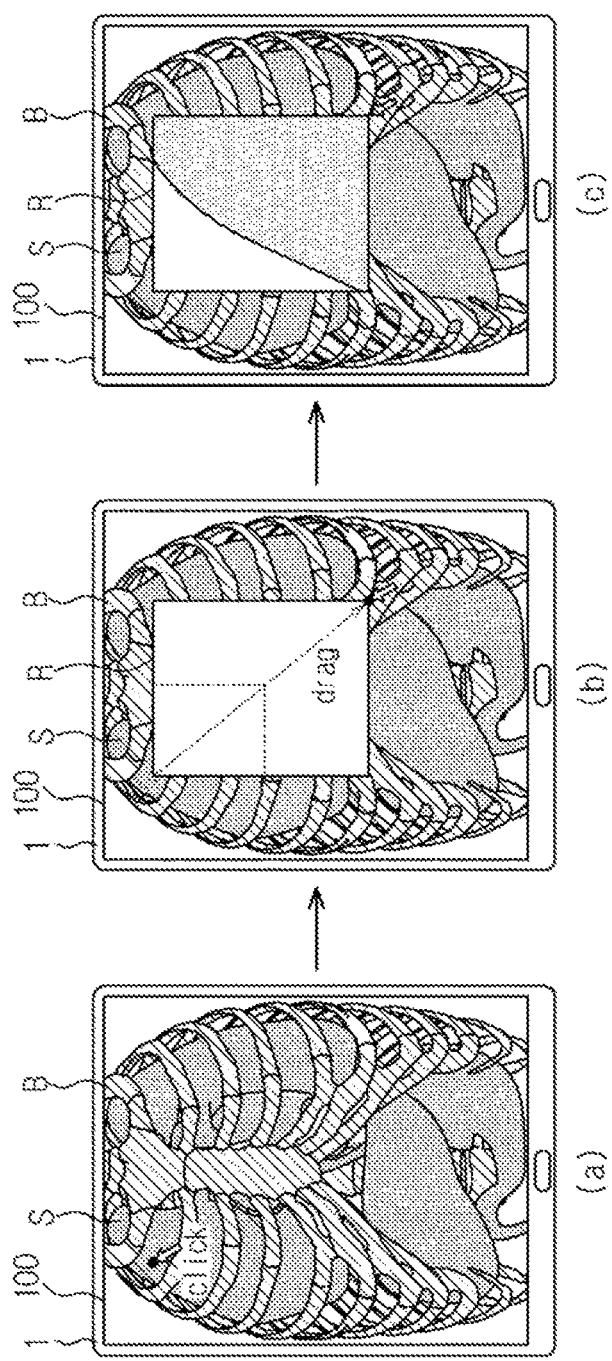

DISPLAY FOR CONVERTING MEDICAL IMAGES AND METHOD OF USE

CROSS-REFERENCE TO RELATED APPLICATION

This application claims priority from Korean Patent Application No. 2013-0162029, filed on Dec. 24, 2013 in the Korean Intellectual Property Office, the entire disclosure of which is incorporated herein by reference.

BACKGROUND

1. Field

Apparatuses and methods consistent with exemplary embodiments related to a display apparatus that displays an image and a method thereof.

2. Description of the Related Art

When checking images using display apparatuses, there are cases in which the images need to be compared with each other. For example, in the medical field there is a need to process an image to generate images with different characteristics in order to find, for example, lesions. In general, images acquired by different medical imaging apparatuses are checked and compared by displaying them on a plurality of display apparatuses.

When a plurality of display apparatuses is used, it is not easy to rapidly compare regions of interest, which may need to be checked while continuously moving one's eyes from one display apparatuses to another. This results in distraction or reduced concentration, when compared to a case in which a single display apparatus is used.

SUMMARY

The exemplary embodiments described herein may overcome the above disadvantages and other disadvantages not described above. Also, an exemplary embodiment is not required to overcome the disadvantages described above, and an exemplary embodiment of the present disclosure may not overcome any of the problems described above.

One or more embodiments provide a display apparatus to display a plurality of different color images having different characteristics of an object on a single screen while gradually and mutually converting the color images and an image display method using the same.

In accordance with an aspect of an exemplary embodiment, there is provided a display apparatus including a memory configured to store a first image and a second image, the first image showing a first characteristic of an object and the second image showing a second characteristic of the object; and a display unit configured to display a gradual conversion of the first image into the second image.

In accordance with an aspect of another exemplary embodiment, there is provided a method of displaying an image using the display apparatus, the method including displaying a first image of an object by using a display unit; and displaying, by using the display unit, a second image having a different characteristic from that of the first image while gradually converting the first image into the second image.

BRIEF DESCRIPTION OF THE DRAWINGS

These and/or other aspects will become apparent and more readily appreciated from the following description of exemplary embodiments, taken in conjunction with the accompanying drawings of which:

FIG. 10 illustrates views for explaining a method of designating a specific region of a display apparatus and displaying the corresponding region as an enlarged image, according to an exemplary embodiment.

DETAILED DESCRIPTION

Figure 1:
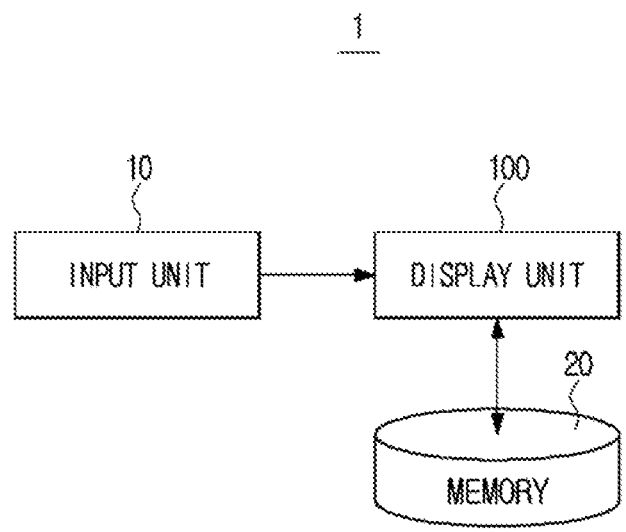
FIG. 1 is a view illustrating configuration of a display apparatus according to an exemplary embodiment.

Certain exemplary embodiments of the present inventive concept will now be described in greater detail with reference to the accompanying drawings. Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

The following detailed description is provided to assist the reader in gaining a comprehensive understanding of the methods, apparatuses, and/or systems described herein. However, various changes, modifications, and equivalents of the methods, apparatuses and/or systems described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 2:
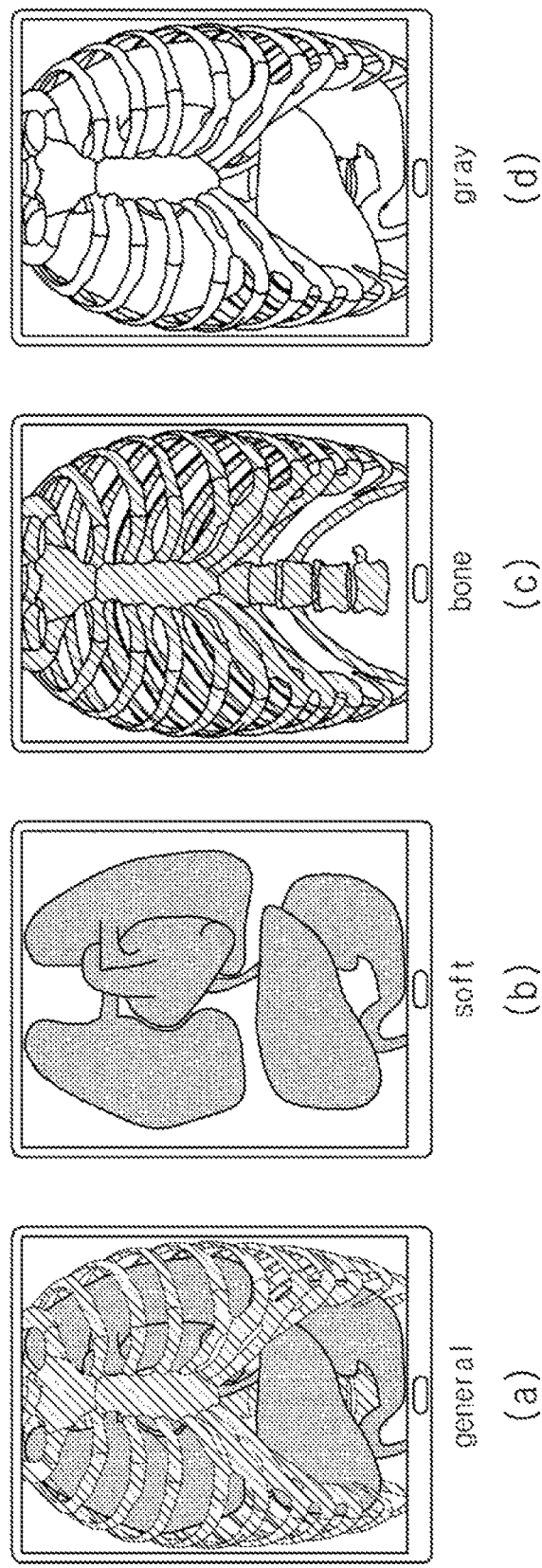
FIG. 2 is a view illustrating medical color images having different characteristics of an object, according to an exemplary embodiment.
Figure 3:
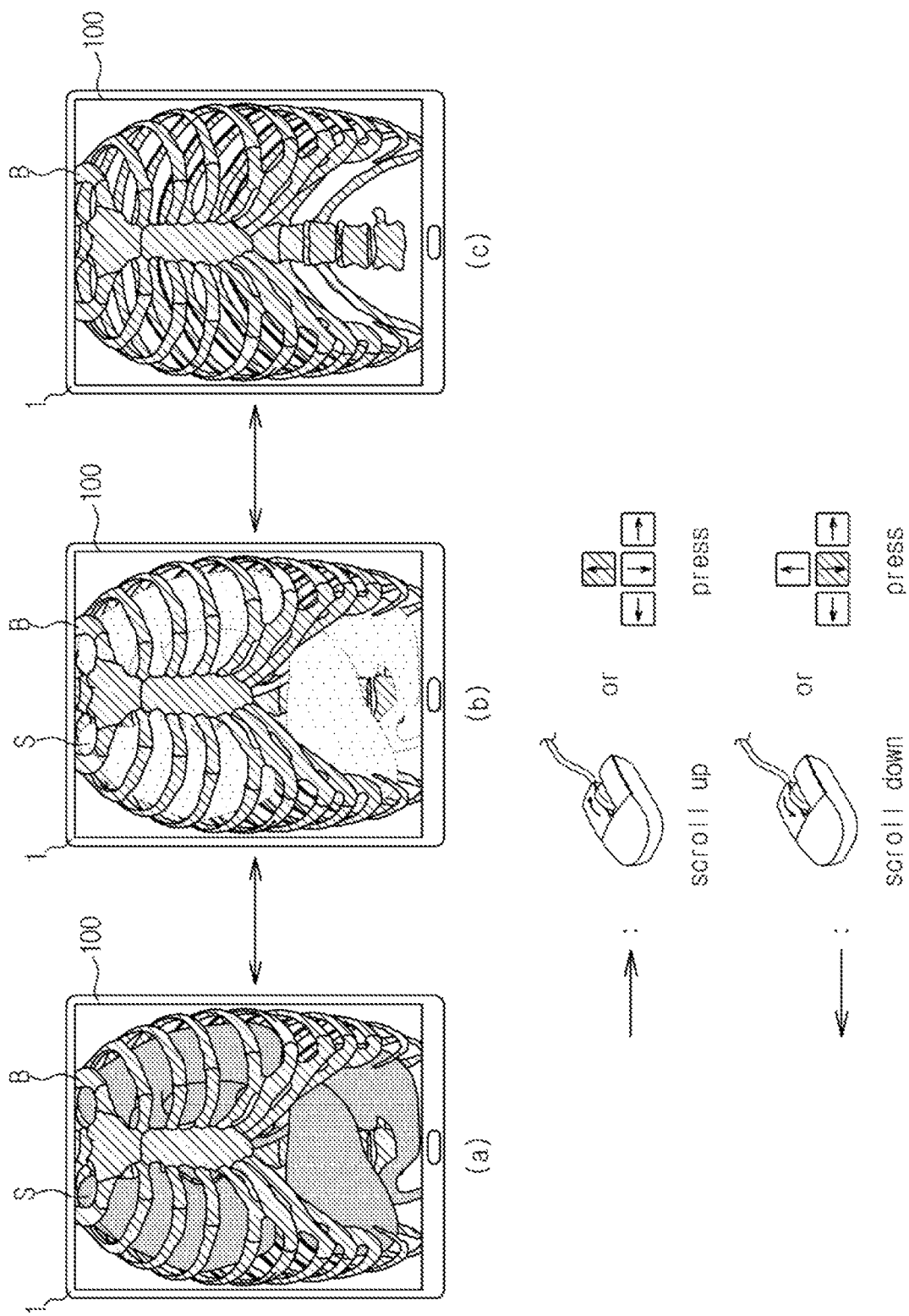
FIGS. 3, 4 and 5 illustrate views illustrating a method of displaying color images having different characteristics while mutually converting the color images using a display apparatus, according to exemplary embodiments.
Figure 4:
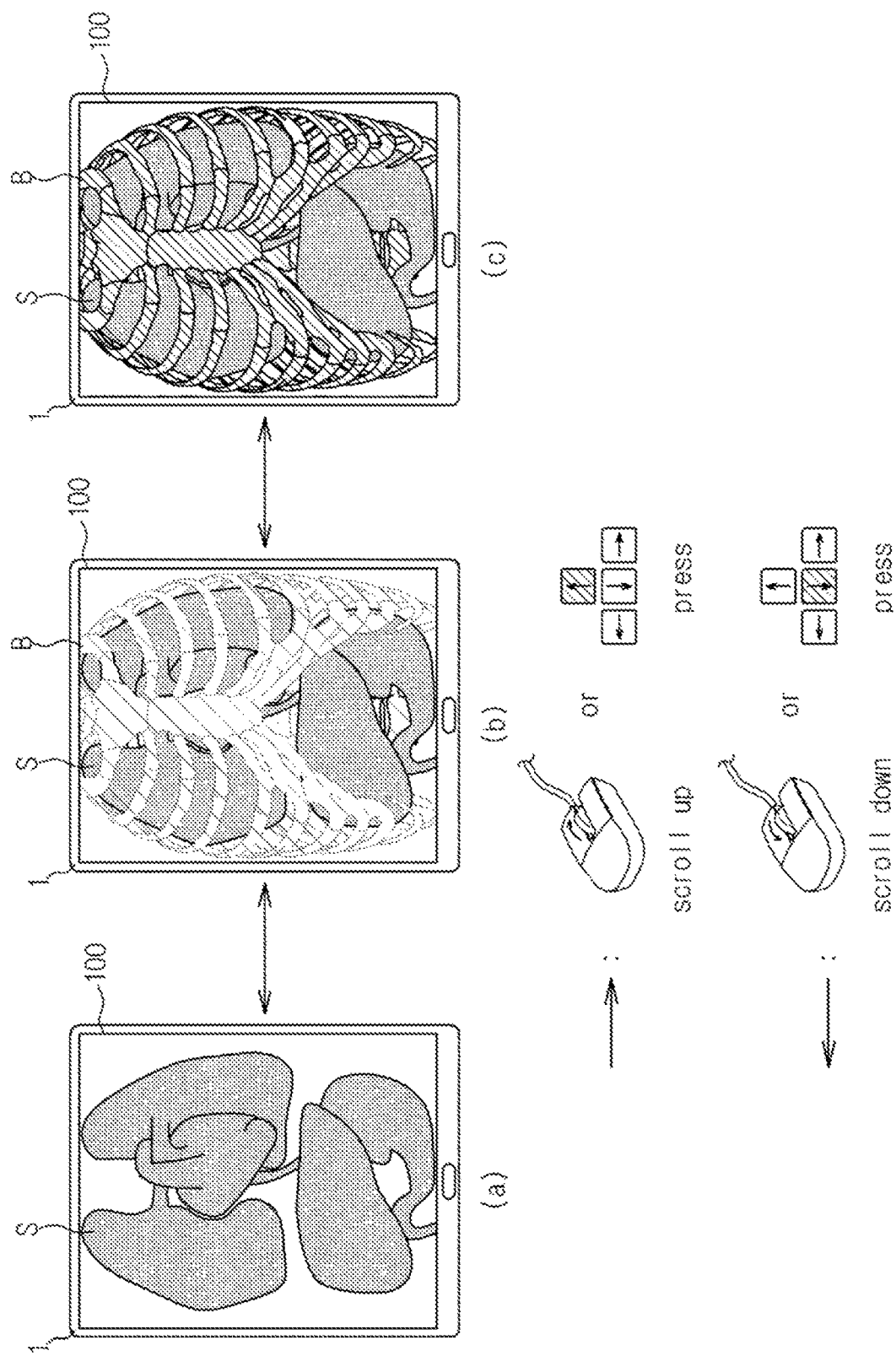
Figure 5:
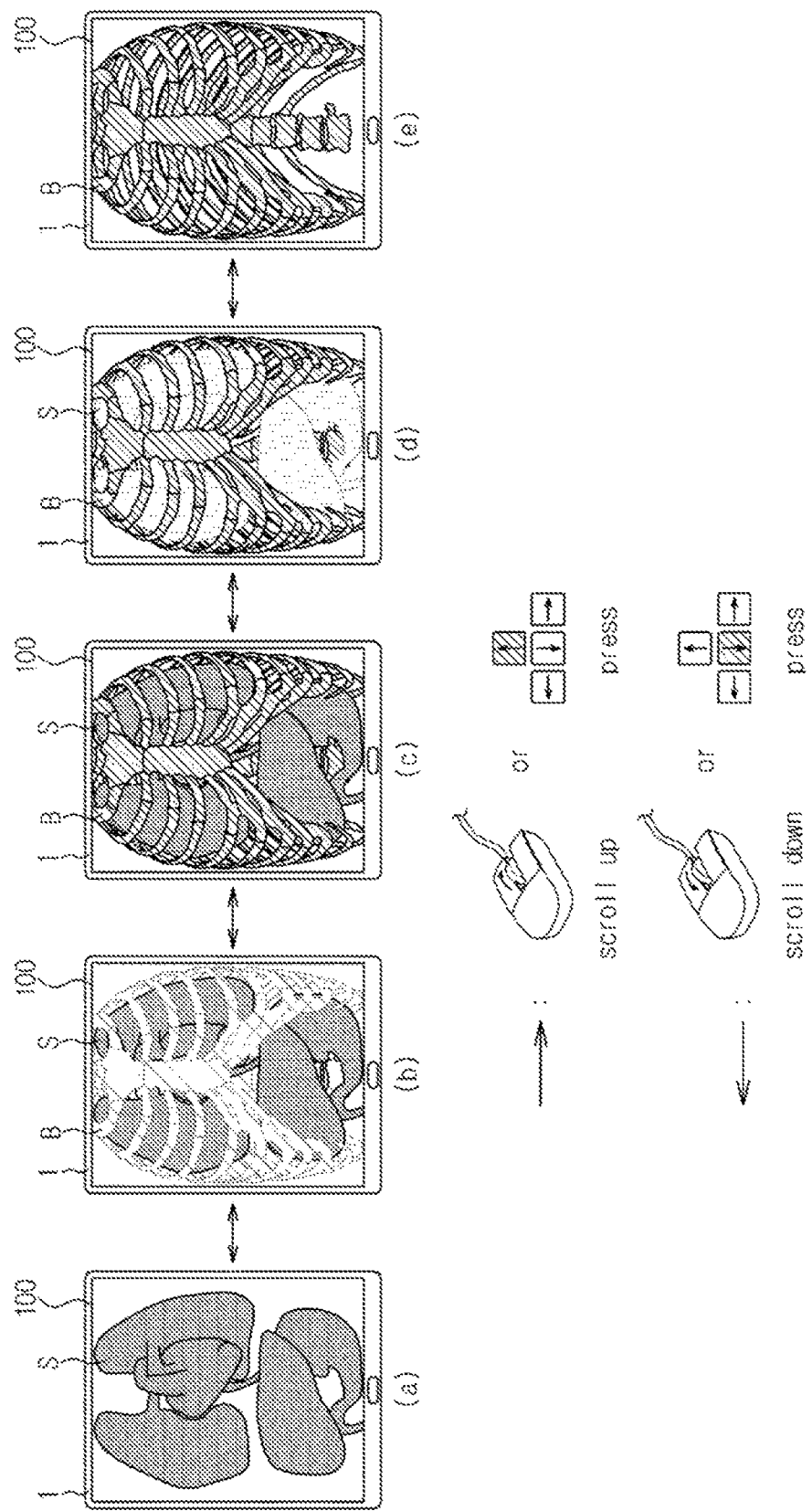

FIG. 1 is a view illustrating configuration of a display apparatus 1 according to an exemplary embodiment. FIG. 2 is a view illustrating medical color images having different characteristics of an object, according to an exemplary embodiment. FIGS. 3 to 5 are views illustrating a method of displaying color images having different characteristics while mutually converting the color images using a display apparatus, according to exemplary embodiments.

As illustrated in FIG. 1, the display apparatus 1 includes a display unit 100 that displays an image, a memory 20 that stores images of an object displayed on the display unit 100, and an input unit 10 through which commands for operation of the display apparatus 1 may be input. The display apparatus 1 may include all apparatuses to display images and examples thereof include, but are not limited to, a commercially available desktop computer, a laptop computer, a tablet computer, and a smart phone.

The display unit 100 includes a screen that displays an image and may display an image using various types of known display methods, and a processor for executing image processing. In addition, the display unit 100 may be embodied using a touch screen through so that a user may input commands by directly touching the display unit 100 and/or by using the input unit 10. In this way, a user may input a desired command to the display device 1 by touching the display unit 100 using a finger or a touch pen. The input unit 10 may include a keyboard, a mouse, a joystick, a trackball, a jog-shuttle, a sound recognition device, a motion recognition device, or the like. The input unit 10 may be integrally formed with the display apparatus 1 and built in the display apparatus 1. In another exemplary embodiment, the input unit 10 may be separately arranged from the display apparatus 1. The input unit 10 arranged independently of the display apparatus 1 may transmit commands input via the input unit 10 to the display apparatus 1 via wireless communication or may be connected to the display apparatus 1 via various types of connectors.

When images are checked, there are cases in which a user needs to check desired information that is contained in color images. In particular, in medicine, a more accurate diagnosis is possible using color images of regions of interest of an object when locating lesions and determining whether lesions are malignant or benign. Hard tissue lesions may overlap with bones and soft tissue lesions may overlap with soft tissues such as organs, therefore when the lesions and the bones or soft tissues are displayed using similar colors it may be difficult to distinguish the lesions from the bones or soft tissues. Thus, in exemplary embodiments of the present disclosure, in order for a user to more accurately acquire desired information, a display apparatus displays color images on a single screen while gradually and continuously converting a color image having a one characteristic into a color image having a another characteristic. Hereinafter, X-ray images used for medical diagnosis will be described to explain the disclosed exemplary embodiments. However, it is understood that technical teachings of the disclosed exemplary embodiments are not limited to medical images and may be applied to all fields requiring comparison and analysis of a plurality of images.

In FIG. 2, images (a), (b) and (c) are colored X-ray images, and image (d) is a grayscale image. Images (a)-(d) illustrate different characteristics of an object, e.g., a chest in this example. Particularly, FIG. 2 shows a general color image (a) showing bones and soft tissues as different colors, a soft tissue color image (b) showing soft tissues alone, a bone color image (c) showing bones alone, and a grayscale image (d) showing bones and soft tissues in different intensities. In color images (a)-(c), different characteristics are displayed using different colors. For example, bones and soft tissues having different degrees of hardness are displayed as different colors. Therefore, it is possible to distinguish bones, which are displayed with one color, from soft tissues, which are displayed with a different color.

FIGS. 3 to 5 are views illustrating a method of displaying, using a single display screen 100, different characteristics of color images (a)-(c) of the object shown in FIG. 2 through mutual conversion between the images.

In this exemplary embodiment, different characteristics of color images (a)-(c) are different anatomical structures, as divided according to a specific standard, shown in the images a particular site of the object. For example, different characteristics in this exemplary embodiment are soft tissues and bones obtained by dividing an anatomical structure shown in a chest X-ray image of an object according to a degree of hardness. A degree of hardness of tissues is only an example of a specific standard that distinguishes characteristics and exemplary embodiments of the present disclosure are not limited thereto. In colored X-ray images (a)-(c), different characteristics such as bones and soft tissues are displayed as different colors as illustrated in FIG. 2.

Referring to colored X-image (a) in FIG. 3, the bones B and soft tissues S are obtained by processing an X-ray image using different energy bands. The bones B and the soft tissues S are displayed on the display unit 100 using different colors. The colored X-ray image (c) in FIG. 3 shows bones B alone.

In response to a command for converting a color image displayed on the display unit 100 into another color image with a different characteristic being input, the display unit 100 converts the displayed color image into another color image that is then displayed. For example, as illustrated in FIG. 3, when, for example, a mouse wheel is scrolled up or a keyboard up arrow key is pressed in a state in which the general color image (a) is displayed on the display unit 100, the general color image (a) is converted into the bone color image (c) and the display unit 100 displays the bone color image (c). Similarly, when the mouse wheel is scrolled down or a keyboard down arrow key is pressed in a state in which the bone color image (c) is displayed on the display unit 100, the bone color image (c) is converted into the general color image (a) and the display unit 100 displays the general color image (a). Commands for converting images are not limited to the above-described examples and may be input via various input devices according to predetermined rules.

In such an image conversion process, the display unit 100 continuously displays changes in characteristics of images during conversion (e.g., image (b)) without directly or instantly converting the general color image (a) into the bone color image (c) or without directly or instantly converting the bone color image (c) into the general color image (a). In response to a command for converting the general color image into the bone color image being input, the display unit 100 displays color of the soft tissues S to gradually become paler and, ultimately, displays the color image showing bones B alone. In another exemplary embodiment, the color of the soft tissues S may be gradually faded and the color of the bones B may be gradually deepened. In response to a command for converting the bone color image (c) into the general color image (a), the display unit 100 displays a conversion process opposite to what has been described above (e.g., image (c) to image (b) to image (a)).

In response to the command for converting the bone color image (c) into the general color image (a) being input during input of the command for converting the general color image (a) into the bone color image (c), the display unit 100 gradually converts the color image during conversion back into the general color image (a) according to the changed command. That is, the display unit 100 performs an image conversion process such that, when an input command is changed, a conversion direction of an image is changed corresponding thereto.

When converting color images, the display unit 100 mutually and gradually coverts color images by using a weighted average for different characteristics of an object, such as bones B and soft tissues S. In response to the command for converting the general color image into the bone color image being input and continued, the display unit 100 continuously reduces a weighted value for the soft tissues S of the color image and displays continuous changes of the color image using a weighted average to which such changes in weighted value are applied. In another exemplary embodiment, the display unit 100 may reduce a weighted value for the soft tissues S, while continuously increasing a weighted value for the bones B and use a weighted average to which such changes in weighted value are applied. Similarly, in response to the command for converting the bone color image (c) into the general color image (a) being input while the command for converting the general color image (a) into the bone color image (c) is being input, the display unit 100 increases a weighted value for the soft tissues S of the color image according to the changed command and displays continuous changes of the color image using a weighted average to which such changes in weighted value are applied. In another exemplary embodiment, the display unit 100 may increase a weighted value for the soft tissues S while reducing a weighted value for the bones B and use a weighted average to which such changes in weighted value are applied. The above-described conversion between color images may be automatically implemented without commands of a user such that, as time elapses, mutual conversion between one color image and another color image is continuously implemented or converting one color image into another color image is implemented.

FIG. 4 illustrates colored X-ray images with different characteristics of an object. Image (c) in FIG. 4 is a colored X-ray image that shows bones B in one color and soft tissues S in another color. Image (a) in FIG. 4 is a colored X-ray image that shows the soft tissues S alone.

In response to a command for converting the color image displayed on the display unit 100 into another color image with a different characteristic being input via, for example, the input unit 10, the display unit 100 converts the displayed color image into another color image and displays the acquired color image. For example, when a mouse wheel is scrolled down or a keyboard down arrow key is pressed in a state in which a general color image (c) is displayed on the display unit 100, the display unit 100 converts the general color image (c) into a soft tissue color image (a) and displays the acquired color image. In addition, when the mouse wheel is scrolled up or a keyboard up arrow key is pressed in a state in which the soft tissue color image is displayed on the display unit 100, the display unit 100 converts the soft tissue color image (a) into the general color image (c) and displays the acquired color image. Commands for converting images are not limited to the above-described examples and may be input via various input devices according to predetermined rules.

In such an image conversion process, the display unit 100 continuously displays changes in characteristics of an image during conversion without directly converting the color image (c) into the color image (a) or without directly converting the color image (a) into the color image (c). That is, the color image (c) gradually transitions via color image (b) into color image (a), and the color image (a) gradually transitions via image (b) into color image (c). In this way, the color transition from image (a) to image (c) or image (c) to image (a) is gradual and continuous (e.g., not instant). In response to a command for converting the general color image (c) into the soft tissue color image (a) being input, the display unit 100 displays color of bones B to gradually become paler (e.g., image (b)) and, ultimately, displays the color image (a) showing the soft tissues S alone. In another exemplary embodiment, the display unit 100 may implement a display operation by gradually fading the color of the bones B and gradually deepening the color of the soft tissues S. In response to a command for converting the soft tissue color image (a) into the general color image (c) being input, the display unit 100 displays a conversion process opposite to what has been described above.

In response to the command for converting the soft tissue color image (a) into the general color image (c) being input during input of the command for converting the general color image (c) into the soft tissue color image (a), the display unit 100 gradually converts the color image during conversion back into the general color image (c) according to the changed command. That is, the display unit 100 performs an image conversion process such that, when an input command is changed, a conversion direction of an image is changed corresponding thereto.

When converting color images, the display unit 100 mutually and gradually coverts color images by using a weighted average for different characteristics of an object, such as bones B and soft tissues S. When the command for converting the general color image into the soft tissue color image is input and continued, the display unit 100 continuously reduces a weighted value for the bones B of the color image and displays continuous changes of the color image using a weighted average to which such changes in weighted value are applied. In another exemplary embodiment, the display unit 100 may reduce a weighted value for the bones B while continuously increasing a weighted value for the soft tissues S and use a weighted average to which such changes in weighted value are applied. On the other hand, when the command for converting the soft tissue color image into the general color image is input while the command for converting the general color image into the soft tissue color image is being input, the display unit 100 increases a weighted value for the bones B of the color image according to the changed command and displays continuous changes of the color image using a weighted average to which such changes in weighted value are applied. In another exemplary embodiment, the display unit 100 may increase a weighted value for the bones B while increasing a weighted value for the soft tissues S and use a weighted average to which such changes in weight value are applied.

Referring to FIG. 5, an image (a), which is a colored X-ray image showing soft tissues S, is displayed on the display unit 100. As described above with respect to FIG. 4, the colored X-ray image (a) of the soft tissues S alone may continually and gradually transition to a colored X-ray image (c) that shows bones B and the soft tissues S as different colors. In the same manner as that described above with respect to FIG. 3, the colored X-ray image (c) of the bones B and the soft tissues S may transition to a colored X-ray image (e) that shows the bones B alone. The image (a) may also continuously and gradually transition to image (e), and vice versa. As described above, the transition direction may change in response to an input from the input unit.

Conversion between color images being displayed on the same display unit 100 has been described with reference to FIGS. 2 to 5. In addition to the conversion between the color images there may be conversion of a color image into a grayscale image or vice versa as illustrated in FIG. 6.

Figure 6:
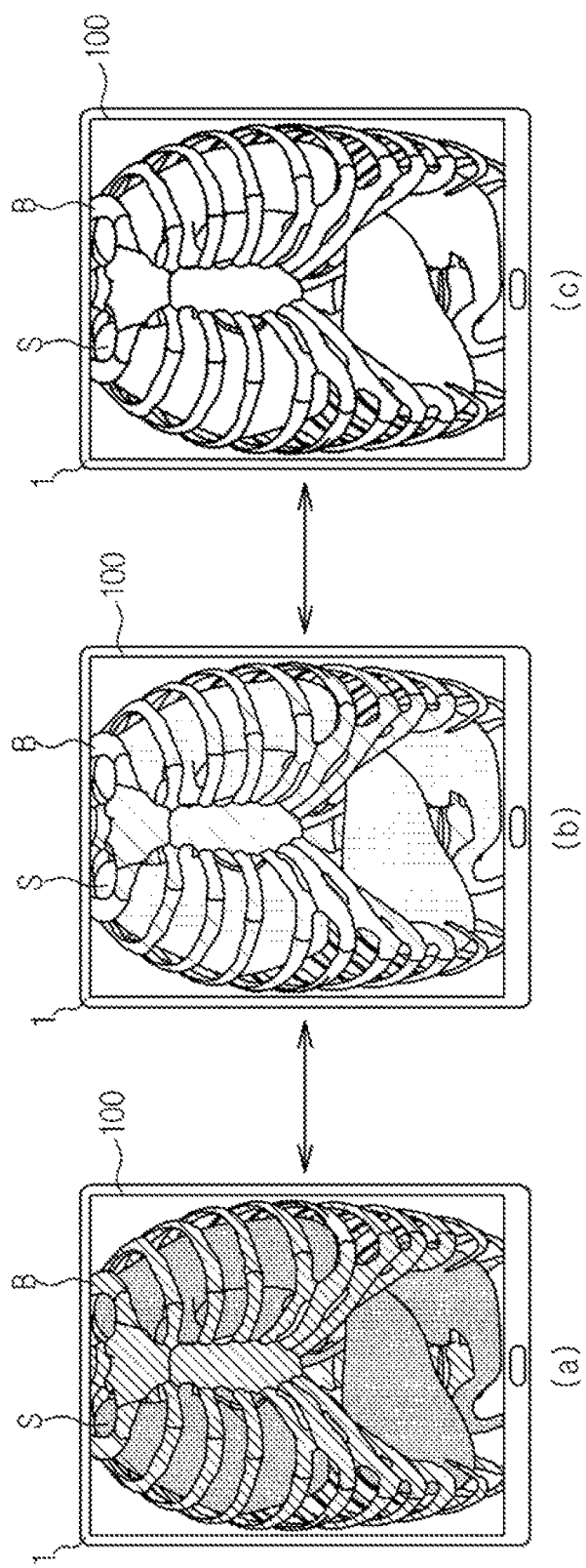
FIG. 6 illustrates views explaining for a method of displaying a color image and a grayscale image while mutually converting the images using a display apparatus, according to an exemplary embodiment.

Referring to FIG. 6, image (a), which is a colored X-ray image of the chest part of an object and shows the bones B and the soft tissues S as different colors, is displayed on the display unit 100. Image (c) is a grayscale image of the chest part of the object.

In response to a command for converting the color image (a) displayed on the display unit 100 into the grayscale image (c) being input via the input unit 10, the display unit 100 converts the displayed color image (a) into the grayscale image (c) showing the same part as that of the color image and displays the grayscale image (c). The command for converting the color image (a) into the grayscale image (c) may be implemented in the same manner as in the command for conversion between color images as described above with respect to FIGS. 3 to 5, in a state in which a mode for conversion between the color image and the grayscale image is selected.

For example, when a mouse wheel is scrolled up or a keyboard up arrow key is pressed in a state in which the color image (a) is displayed on the display unit 100, the display unit 100 converts the color image (a) into the grayscale image (c) and displays the grayscale image (c). In addition, when the mouse wheel is scrolled down or a keyboard down arrow key is pressed in a state in which the grayscale image (c) is displayed on the display unit 100, the display unit 100 converts the grayscale image (c) into the color image (a) and displays the color image (a). Commands for converting images are not limited to the above-described examples and may be input via various input devices according to predetermined rules. In such an image conversion process, the display unit 100 continuously displays changes in characteristics of an image during conversion without directly or instantly converting the color image (a) into the grayscale image (c) or without directly or instantly converting the grayscale image (c) into the color image (a). In response to the command for converting the color image into the grayscale image being input, the display unit 100 gradually reduces chroma of the color image (a) and, ultimately, displays the grayscale image (c) in achromatic colors. In response to a command for converting the grayscale image (c) into the color image (a) being input, the display unit 100 displays a conversion process opposite to what has been described above.

In response to the command for converting the grayscale image into the color image (a) being input during input of the command for converting the color image (a) into the grayscale image (c), the display unit 100 gradually converts the color image (a) having undergone conversion into the grayscale image (c) back into the color image (a) by gradually increasing chroma of the image during conversion according to the changed command. That is, the display unit 100 converts an image such that, when an input command is changed, a conversion direction of the image is changed correspondingly thereto.

In addition to mutual conversion between color images with different characteristics or between the color image and the grayscale image on a single display screen as illustrated in FIGS. 3 to 6, exemplary embodiments of the present disclosure provide methods of checking an object on a single screen by dividing an image of the same object into color images with different characteristics.

Figure 7:
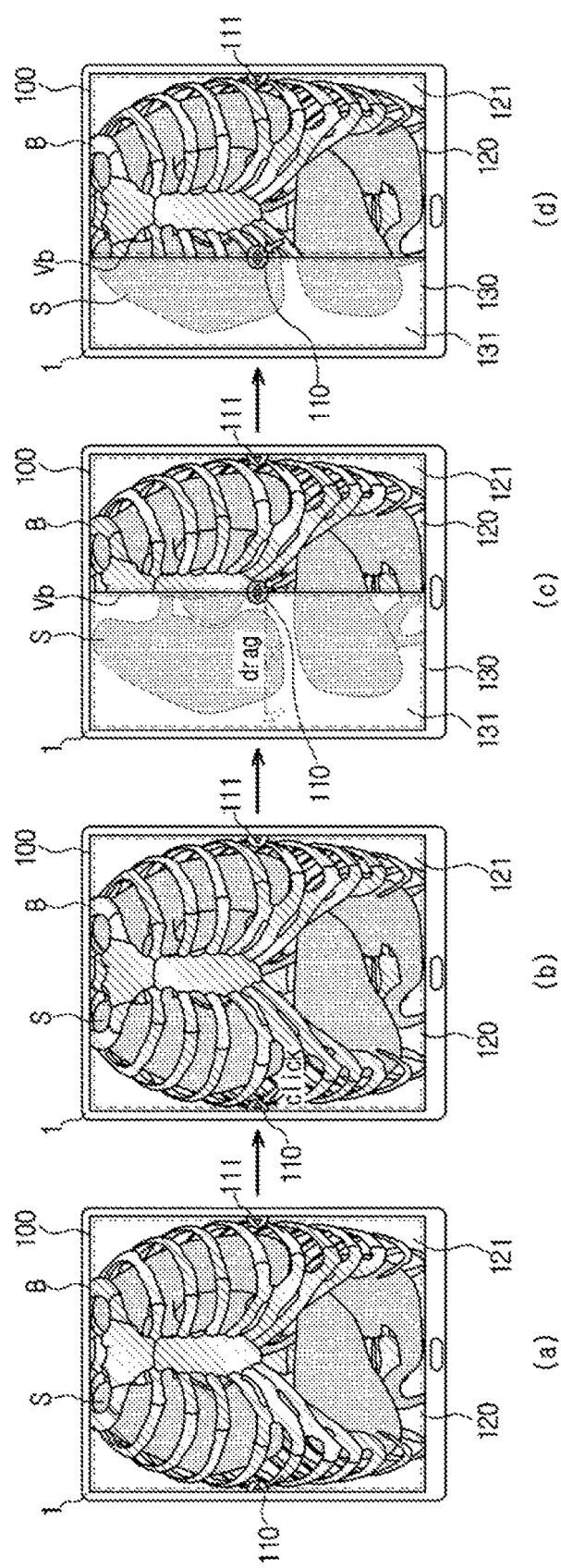
FIGS. 7 and 8 illustrate views for explaining methods of displaying color images by dividing a screen of a display apparatus, according to exemplary embodiments.
Figure 8:
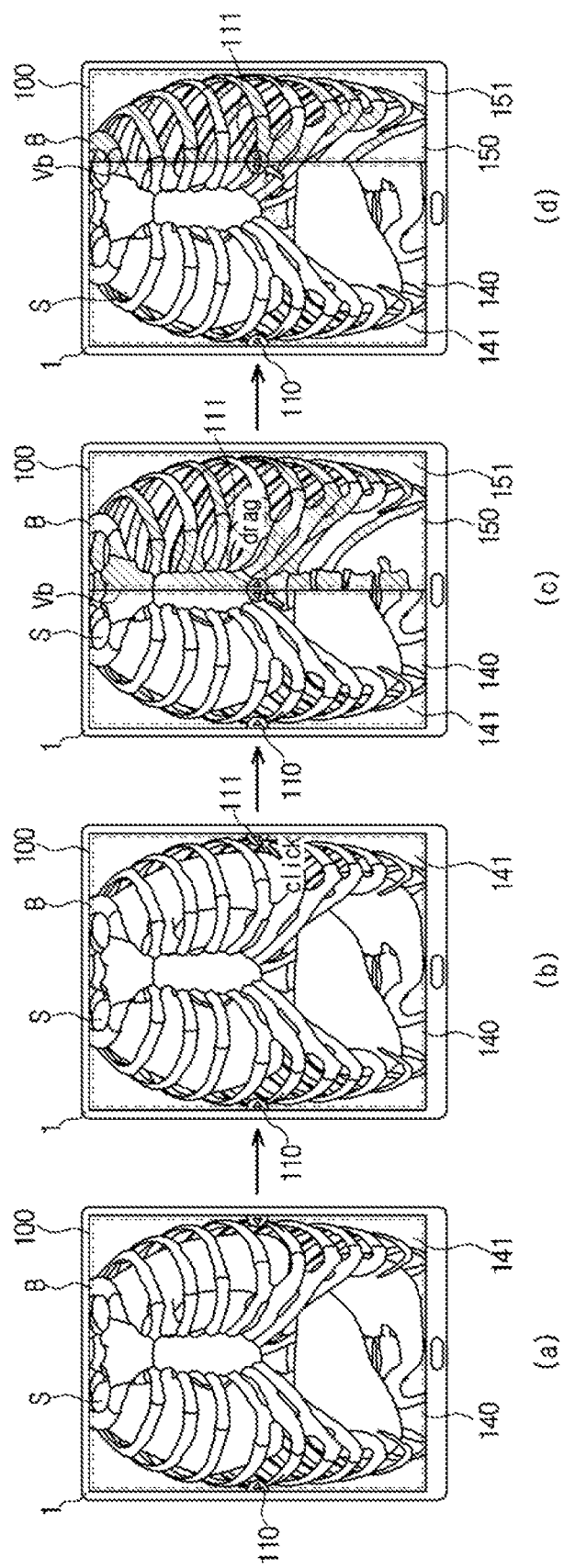

FIGS. 7 and 8 illustrate methods of displaying color images by dividing a screen of a display apparatus, according to exemplary embodiments of the present disclosure.

FIG. 7(a) illustrates a state prior to screen division in which a first region 120 to display a general color image 121 showing bones B and soft tissues S in different colors forms the entire display area of the display unit 100. The image displayed in the first region 120 prior to screen division is not limited to the general color image 121, may be images with different characteristics of a certain region of the same object, such as the bone X-ray image, the soft tissue X-ray image, or the like among the color images illustrated in FIG. 2 and may be selected by a user.

In FIG. 8, (a) illustrates a state prior to screen division in which a first region 140 to display a general grayscale image 141 showing both bones B and soft tissues S forms the entire display area of the display unit 100. The image displayed in the first region 140 prior to screen division is not limited to the general grayscale image 141, may be grayscale images with different characteristics of a certain region of the same object, such as a grayscale image showing the bones alone, a grayscale image showing the soft tissues S alone, or the like, and may be selected by a user. FIG. 8 illustrate the grayscale image 141 in the first region 140 unlike what is illustrated in FIG. 7, while illustrating a color image displayed in a second region obtained by dividing the screen of the display unit 100 as in FIG. 7. Thus, a method of generating a second region by dividing the screen and displaying a color image in the second region will be described with reference to FIG. 7 only.

When a user clicks or touches a marker 110 displayed on the left side of the display unit 100 as illustrated in FIG. 7(b) and a command to drag the marker 110 to the right side is input as illustrated in FIG. 7(c), the screen is divided into the first region 120 and a second region 130. When the marker 110 is clicked or touched, a vertical boundary line Vb passing through the marker 110 is formed. Of course the boundary line can horizontal, diagonal, etc. However, this feature will be explained by referring to a Vertical boundary line Vb. When the marker 110 is dragged, the vertical boundary line Vb moves together with the marker 110 in a direction in which the marker 110 is dragged. The vertical boundary line Vb corresponds to a boundary between the first and second regions 120 and 130.

As illustrated in FIGS. 7(a) to 7(d), the marker 110 has a symbol such as an arrow and thus may indicate a movable direction. In addition, clicking and dragging of the marker 110 may be performed by directly touching the marker 110 using a touch member such as a finger or a touch pen or through the aforementioned input unit 10 such as a mouse, a keyboard, a track ball, a joystick, a jog-shuttle, a voice recognition device, or a motion recognition device.

As illustrated in FIG. 7(c), when the vertical boundary line Vb is moved to the right side by clicking and dragging the marker 110 to the right side of the display unit 100, a screen share of the first region 120 is decreased and a screen share of the second region 130 is increased. As the screen share of the first region 120 decreases, a proportion of the chest part of the object on the general color image 121 displayed in the first region 120 also correspondingly decreases. In FIG. 7(a), the entirety of the object is shown as the general color image 121. In FIG. 7(c), only the right half of the chest part of the object is displayed as the general color image 121, and the other half of the chest part is displayed in the second region 130 as a soft tissue color image 131. A sum of the first region 120 in which the general color image 121 is displayed and the second region 130 in which the soft tissue color image 131 is displayed corresponds to the entirety of the chest part of the object.

As illustrated in FIG. 7(d), when the vertical boundary line Vb is moved to the second region 130 by clicking and dragging the marker 110 to the second region 130, the decreased screen share of the first region 120 increases again, while the increased screen share of the second region 130 decreases again. As the screen share of the first region 120 increases, the proportion of the chest part of the object shown on the general color image 121 displayed in the first region 120 also correspondingly increases. While FIG. 7(c) illustrates that the general color image 121 shows only the right half of the chest part of the object, FIG. 7(d) illustrates that about ⅔ of the object is displayed as the general color image 121. The remaining ⅓ of the object is displayed as the soft tissue color image 131 displayed in the second region 130. Similar to what is illustrated in FIG. 7(c), the sum of the first region 120 in which the general color image 121 is displayed and the second region 130 in which the soft tissue color image 131 is displayed corresponds to the entire chest part of the object.

As illustrated in FIGS. 7(c) and 7(d), the soft tissue color image 131 is only given as an example and the second image 131 displayed in the second region 130 may include a color image with a different characteristic of the same region as that of the object shown on the general color image 121, e.g., a bone color image.

As illustrated in FIGS. 7(c) and 7(d), the screen shares of the first region 120 and the second region 130 vary according to movement of the marker 110 and, accordingly, the proportions of the chest part of the object shown on the general color image 121 and the soft tissue color image 131 also vary. However, regardless of the proportions of the chest part of the object shown in the general color image 121 and the soft tissue color image 131, the general color image 121 and the soft tissue color image 131 naturally match each other at the vertical boundary line Vb. The images matching each other represent the entire image of the photographed site of the object as in the case of the image prior to screen division.

Using this method, a user may move the marker 110 near a region of interest to be observed and easily and quickly check color images with different characteristics of the region of interest in an alternating manner. In other words, a user may easily and seamlessly compare different color images, each of which has an intrinsic characteristic, in a single display apparatus instead of a plurality of display apparatuses.

In response to a command for converting the image displayed in the first or second region being input by a user, as described above with reference to FIGS. 3 to 5, the display unit 100 may gradually convert the color image displayed in the first or second region into a color image with a different characteristic.

Figure 9:
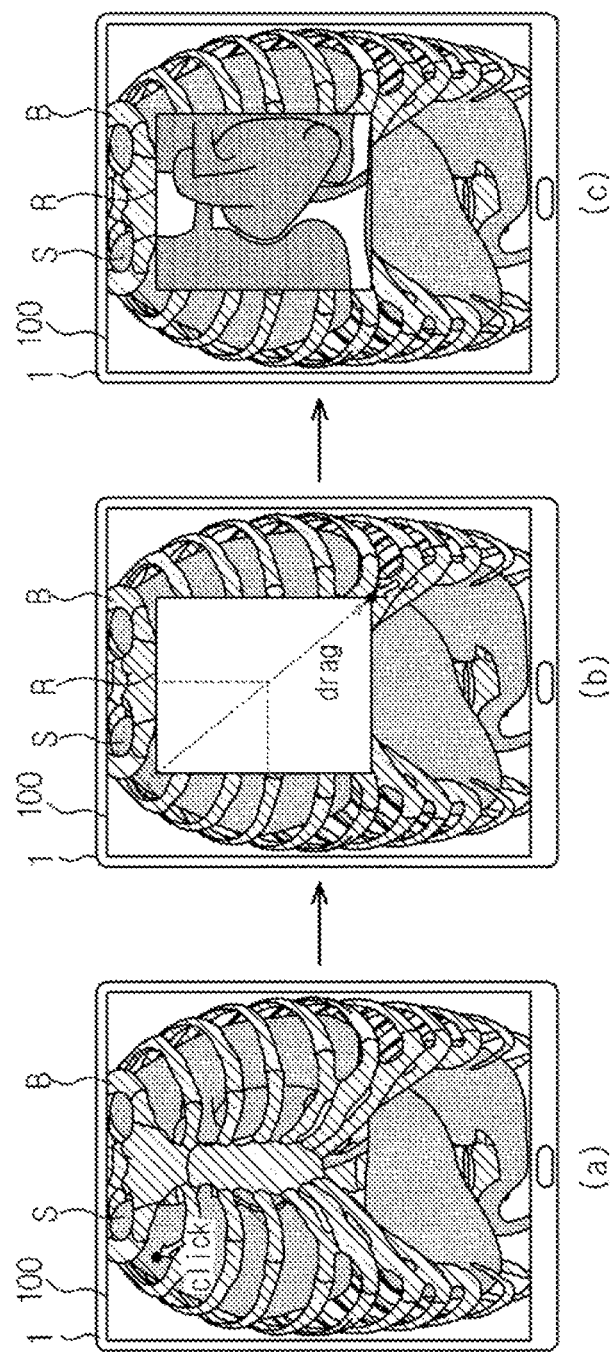
FIG. 9 illustrates views for explaining a method of designating a specific region of a display apparatus and displaying the corresponding region as a color image with a different characteristic, according to an exemplary embodiment.

In addition to the method of respectively displaying color images with different characteristics in regions obtained by dividing the screen of the display unit 100 using the method described above with reference to FIGS. 7 and 8, as illustrated in FIG. 9, a specific region of the screen of the display unit 100 may be designated as a region of interest and the corresponding region may be displayed as a color image with a different characteristic.

FIG. 9 illustrates views for explaining a method of designating a specific region of the display apparatus 1 and displaying the corresponding region as a color image with a different characteristic, according to an exemplary embodiment of the present disclosure. FIG. 10 illustrates views for explaining a method of designating a specific region of the display apparatus 1 and displaying the corresponding region as an enlarged image, according to an exemplary embodiment of the present disclosure.

As illustrated in FIGS. 9 (a) and (b), a user designates a region of interest by clicking (a) and dragging (b) a predetermined position in the vicinity of the region of interest. In general, a rectangle having a drag line as a diagonal line thereof is formed in the dragging direction and the rectangular area formed in this way may be designated as a region of interest. This process is only given as an example and the region of interest may also be designated using various other methods. For example, the shape and size of the region of interest may be specified by touching a predetermined position near the region of interest and drawing the shape of a region to be enlarged with a finger or a touch pen. As illustrated in FIG. 9(c), when the region of interest is designated, the region of interest may be displayed as a soft tissue color image, which is a color image with a different characteristic of an object, unlike a non-region of interest displayed as a general color image. In this regard, the soft tissue color image is only given as an example and the region of interest may also be displayed as a bone color image.

In addition, as illustrated in FIG. 10, when a region of interest is designated, the display unit 100 may enlarge a color image with a different characteristic displayed in the region of interest and display the enlarged color image. When designation of the region of interest is completed, the color image to be displayed in the region of interest is enlarged at a predetermined magnification and the enlarged color image is displayed. Magnification for enlargement may be variously preset and stored in the memory 20, and a user may determine an enlargement degree of an image by selecting a desired magnification for enlargement.

In addition, in response to an image conversion command for an image displayed in the designated region of interest being input by a user, as described above with reference to FIGS. 3 to 5, the display unit 100 may gradually convert a soft tissue color image displayed in the region of interest into a bone color image.

Although FIGS. 3 to 10 illustrate a method of displaying color images with different characteristics acquired using an X-ray imaging apparatus, color images of the same site of the same object, acquired using different modalities of medical imaging apparatuses, may be displayed.

In addition, the display unit 100 may be provided at an end thereof with an interface to allow a user to select settings related to manipulation of the display unit 100, such as selection of images, display options, and the like.

According to the exemplary embodiments, instead of using a plurality of display apparatuses, a single display apparatus displays images, e.g., color medical images, with different characteristics while mutually converting the images and, accordingly, presence or absence and characteristics of lesions at the same position may be more accurately checked.

In addition, since the single display apparatus is used, it is desired in terms of space configuration of a diagnostic imaging system.

Although a few exemplary embodiments of the present disclosure have been shown and described, it would be appreciated by those skilled in the art that changes may be made in these exemplary embodiments without departing from the principles and spirit of the inventive concept, the scope of which is defined in the claims and their equivalents.

The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An X-ray imaging apparatus comprising: a processor configured to process images;
   a memory configured to store a first color X-ray image and a second color X-ray image of a part of a same object, the first color X-ray image showing a first characteristic of the part of the same object and the second color X-ray image showing a second characteristic of the part of the same object, wherein the second color X-ray image is a different type of image than the first color X-ray image;
   an input device configured to receive a conversion command for gradually converting the first color X-ray image into the second color X-ray image; and
   a display,
   wherein the processor is configured to control the display to display a gradual conversion, which occurs over a period of time, of the first color X-ray image into the second color X-ray image in response to the conversion command, such that only the second color X-ray image is displayed after the period of time elapses,
   wherein the processor is further configured to control the display to display a transition image during the period of time that includes at least one characteristic of the first color X-ray image and at least one characteristic of the second color X-ray image, and
   wherein the processor is configured to control the display to display the gradual conversion of the first color X-ray image into the second color X-ray image in accordance with a predetermined rate.

2. The X-ray imaging apparatus according to claim 1, wherein the processor is configured to control the display to display the first color X-ray image and the second color X-ray image while gradually and mutually converting, over a period of time, the first color X-ray image into the second color X-ray image or the second color X-ray image into the first color X-ray image by using a weighted average for the first and second characteristics of the first and second color X-ray images, respectively.

3. The X-ray imaging apparatus according to claim 1, wherein the processor is configured to change a weighted value for the first characteristic of the first color X-ray image and a weighted value for the second characteristic of the second color X-ray image so that the weighted value for the first characteristic and the weighted value for the second characteristic change in inverse proportion to each other, and the processor is configured to control the display to display the first and second color X-ray images while gradually and mutually converting, over a period of time, the first and second color X-ray images using a weighted average for the first and second characteristics of the first and second color X-ray images, respectively.

4. The X-ray imaging apparatus according to claim 1, wherein the processor is configured to, in response to the conversion command, change a first weighted value for the first characteristic of the first color X-ray image and a second weighted value for the second characteristic of the second color X-ray image so that the weighted value for the first characteristic and the weighted value for the second characteristic change in inverse proportion to each other and the processor is configured to control the display to display the first and second color X-ray images while gradually and mutually converting, over a period of time, the first color X-ray image into the second color X-ray image or the second color X-ray image into the first color X-ray image by using a weighted average for the first and second characteristics of the first and second images, respectively.

5. The X-ray imaging apparatus according to claim 1, wherein in response to the input device receiving a command for simultaneous display of the first and second color X-ray images, the processor is configured to control the display to divide a screen into a first region and a second region in accordance with the command for simultaneous display, a first portion of the object being shown by the first color X-ray image in the first region, and a second portion of the object being shown by the second color X-ray image in the second region.

6. The X-ray imaging apparatus according to claim 5, wherein the processor is configured to control the display seamlessly display the object as a plurality of portions including the first and second portions of the object.

7. The X-ray imaging apparatus according to claim 1, wherein the input device is a touch screen included in the display and is configured to receive the conversion command through the touch screen.

8. A method of displaying an image using an X-ray imaging apparatus, the method comprising:
   displaying a first color X-ray image of a part of an object on a screen of a display of the X-ray imaging apparatus;
   receiving, by an input device of the X-ray imaging apparatus, a conversion command for gradually converting the first color X-ray image into a second color X-ray image of the part of the same object;
   displaying, on the screen of the display, a transition image during a period of time that includes at least one characteristic of the first color X-ray image and at least one characteristic of the second color X-ray image, in response to the conversion command; and
   gradually converting, over the period of time, the transition image into the second color X-ray image in response to the conversion command, such that only the second color X-ray image is displayed after the period of time elapses,
   wherein the second color X-ray image is a different type of image than the first color X-ray image, and
   wherein the gradually converting comprises displaying a gradual conversion of the transition image into the second color X-ray image according to a predetermined rate.

9. The method according to claim 8, wherein the gradually converting comprises changing a weighted value for a first characteristic of the first color X-ray image and a weighted value for a second characteristic of the second color X-ray image so that the weighted value for the first characteristic and the weighted value for the second characteristic change in inverse proportion to each other and displaying the second color X-ray image while gradually and mutually converting, over a period of time, the first and second color X-ray images using a weighted average for the characteristics of the first and second color X-ray images.

10. The method according to claim 8, further comprising:
receiving, by the input device of the X-ray imaging apparatus, a command for simultaneously displaying of the first and second color X-ray images; and
dividing the screen, in accordance with the command, into a first region and a second region, a first portion of the object being shown by the first color X-ray image in the first region, and a second portion of the object being shown by the second color X-ray image in the second region.

11. The method according to claim 10, further comprising seamlessly displaying on the screen the object as a plurality of portions including the first and second portions of the object.

12. The X-ray imaging apparatus according to claim 1, wherein the first color X-ray image corresponds to one of a representation of bone, or a representation of soft tissue; and
the second color X-ray image is the other of the representation of bone or soft tissue.

13. The method according to claim 8, wherein the first color X-ray image corresponds to one of a representation of bone, or a representation of soft tissue; and
the second color X-ray image is the other of the representation of bone or soft tissue.

14. The X-ray imaging apparatus according to claim 1, wherein the first color X-ray image corresponds to one of a first color representation of the object, or a second color representation of the object; and
the second color X-ray image is the other of the first and second color representations of the object.

15. The method according to claim 8, wherein the first color X-ray image corresponds to one of a first color representation of the object, or a second color representation of the object; and
the second color X-ray image is the other of the first and second color representations of the object.

16. The X-ray imaging apparatus according to claim 1, wherein the first color X-ray image corresponds to one of a color representation of the object, or a grayscale representation of the object; and
the second color X-ray image is the other of a color representation of the object, or a grayscale representation of the object.

17. The method according to claim 8, wherein the first color X-ray image corresponds to one of a color representation of the object, or a grayscale representation of the object; and
the second color X-ray image is the other of a color representation of the object, or a grayscale representation of the object.

18. The X-ray imaging apparatus according to claim 1, wherein the processor transforms the entirety of the first color X-ray image into the entirety of the second color X-ray image.

19. The method according to claim 8, further comprising transforming the entirety of the first color X-ray image into the entirety of the second color X-ray image.

20. A display apparatus comprising: a processor configured to process images;
a memory configured to store a first color image and a second color image of a part of a same object acquired using different modalities of medical imaging apparatuses, the first color image showing a first characteristic of the part of the same object and the second color image showing a second characteristic of the part of the same object, wherein the second color image is a different type of image than the first color image;
an input device configured to receive a conversion command for gradually converting the first color image into the second color image; and
a display,
wherein the processor is configured to control the display to display a gradual conversion, which occurs over a period of time, of the first color image into the second color image in response to the conversion command, such that only the second color image is displayed after the period of time elapses,
wherein the processor is further configured to control the display to display a transition image during the period of time that includes at least one characteristic of the first color image and at least one characteristic of the second color image, and wherein the processor is configured to control the display to display the gradual conversion of the first color image into the second color image in accordance with a predetermined rate.

21. A method of displaying an image using a display apparatus, the method comprising:
displaying a first color image of a part of an object on a screen of a display of the display apparatus;
receiving, by an input device of the display apparatus, a conversion command for gradually converting the first color image into a second color image of the part of the same object;
displaying, on the screen of the display, a transition image during a period of time that includes at least one characteristic of the first color image and at least one characteristic of the second color image, in response to the conversion command; and
gradually converting, over the period of time, the transition image into the second color image in response to the conversion command, such that only the second color image is displayed after the period of time elapses,
wherein the first color image and the second color image are acquired using different modalities of medical imaging apparatuses, and the second color image is a different type of image than the first color image, and wherein the gradually converting comprises displaying a gradual conversion of the transition image into the second color image according to a predetermined rate.

* * * * *